US010253074B2

(12) United States Patent
Johnson et al.

(10) Patent No.: US 10,253,074 B2
(45) Date of Patent: Apr. 9, 2019

(54) **NONTOXIGENIC *CLOSTRIDIUM BOTULINUM* STRAINS AND USES THEREOF**

(75) Inventors: Eric A. Johnson, Madison, WI (US); Marite Bradshaw, Madison, WI (US); Kristin M. Marshall, South Beloit, IL (US)

(73) Assignee: Wisonsin Alumni Research Foundation, Madison, WI (US)

( * ) Notice: Subject to any disclaimer, the term of this patent is extended or adjusted under 35 U.S.C. 154(b) by 1378 days.

(21) Appl. No.: 12/550,692

(22) Filed: Aug. 31, 2009

(65) Prior Publication Data

US 2010/0112149 A1 May 6, 2010

Related U.S. Application Data

(60) Provisional application No. 61/093,194, filed on Aug. 29, 2008.

(51) Int. Cl.
*C12N 15/10* (2006.01)
*C07K 14/33* (2006.01)
*C12N 15/09* (2006.01)
*C12N 15/87* (2006.01)

(52) U.S. Cl.
CPC .............. *C07K 14/33* (2013.01); *C12N 15/09* (2013.01)

(58) Field of Classification Search
CPC ................................ C07K 14/33; G01N 33/02
USPC .......................................................... 426/232
See application file for complete search history.

(56) References Cited

U.S. PATENT DOCUMENTS 5,955,368 A * 9/1999 Johnson et al. .............. 435/488

2008/0274480 A1 * 11/2008 Atassi .......................... 435/7.21

OTHER PUBLICATIONS

Lee, Correlation of Toxic and Non-toxic Strains of Clostridium botulinum by DNA Composition and Homology, J. Gen. Mirobiol. (1970) 60, 117-123.*
DeCarvalho, Botuliunum Toxin, (May 30, 2014), accessed at http://www.toxipedia.org/display/toxipedia/Botulinum+Toxin.*
Heap, et al., "The ClosTron: a unique gene knock-out system for the genus *Clostridium*", (2007) J. Micr. Methods 70:452-464.
Heap, et al., "The development of genetic knock-out systems for Clostridia, in Brüggemann and Gottschalk, ed., Molecular Biology in the Post-genomic Era", (Norwich U.K.: Horizon Scientific Press) 2009; pp. 179-198.
Public Health England, Bacteria and Mycoplasmas Detail, Bacteria Collection: Clostridium botulinum, dated Sep. 22, 2015, 2 pages.
Clostridium botulinum Str. ATCC 7948—Clipboard—BioSample—NCBI; http://www.ncbi.nlm.nih.gov/biosample/clipboard[Sep. 23, 2015 2:10:52 PM], 2 pages.
Keto-Timonen, et al. "Identification of *Clostridium* Species and DNA Fingerprinting of *Clostridium perfringens* by Amplified Fragment Length Polymorphism Analysis" Journal of Clinical Microbiology, vol. 44, No. 11, Nov. 2006, p. 4057-4065.

(Continued)

*Primary Examiner* — Michele L Jacobson
*Assistant Examiner* — Philip A. Dubois
(74) *Attorney, Agent, or Firm* — Quarles & Brady LLP (57) ABSTRACT

A mutant strain of the bacterium *Clostridium botulinum* having an inactivated botulinal neurotoxin gene is disclosed. The mutant strain contains an artificially created and inserted modified intron vector between nucleotides 580 and 581 of the sense strand of the gene. The mutant strain can be used in microbiological challenge testing of foods and food processing methods.

11 Claims, 6 Drawing Sheets

Specification includes a Sequence Listing.

(56) References Cited

OTHER PUBLICATIONS

Nevas, et al. "Diversity of Proteolytic Clostridium botulinum Strains, Determined by a Pulsed-Field Gel Electrophoresis Approach" Applied and Environmental Microbiology, vol. 71, No. 3, Mar. 2005, p. 1311-1317.

Martinez-Abarca, et al. "Group II introns in the bacterial world" Molecular Microbiology, 38(5):917-926.
Mills et al., 1996, Splicing of a Group II intron involved in the conjugative transfer of pRS01 in Lactococci, Journal of Bacteriology, 178(12):3531-3538.
GenBank ID U50902, based on Mills et al. 1996, sequence information updated on Mar. 5, 2007.
Cousineau et al., 1998, Retrohoming of a bacterial group II intron: mobility via complete reverse splicing, independent of homologous DNA recombination, Cell, 94:451-462.
Karberg et al., 2001, Group II introns as controllable gene targeting vectors for genetic manipulation of bacteria, Nature Biotechnology, 19:1162-1167.

* cited by examiner

NONTOXIGENIC *CLOSTRIDIUM BOTULINUM* STRAINS AND USES THEREOF

CROSS-REFERENCE TO RELATED APPLICATIONS

This application claims the benefit of U.S. Provisional Application No. 61/093,194, filed on Aug. 29, 2008, which is incorporated by reference herein in its entirety.

FIELD OF THE INVENTION

The present invention generally relates to mutant strains of the bacterium *Clostridium botulinum*. Specifically, the present invention relates to stable mutant strains of *Clostridium botulinum* wherein the wild type botulinal neurotoxin gene has been inactivated. The invention also relates to the use of these mutant strains in microbiological challenge testing.

BACKGROUND OF THE INVENTION

*Clostridium botulinum* produces the most poisonous toxin known and is a perennial concern to the food industry and to regulatory agencies due to the potential threat of food borne botulism. An ongoing trend within the Food Industry is the development of foods that have natural ingredients, that are free of preservatives, and that are produced under mild processing conditions. The botulinal safety of such foods can be an issue, and several outbreaks of botulism have occurred due to changes in processing procedures and formulations.

To ensure the botulinal safety of foods, rigorous microbiological challenge testing has been routinely performed using a mouse bioassay and/or in vitro assays. Microbiological challenge testing is a useful tool for determining the ability of a food to support the growth of spoilage organisms or pathogens. Microbiological challenge tests also play an important role in the validation of processes that are intended to kill or attenuate a target organism or group of target organisms. An appropriately designed microbiological challenge test will validate that a specific process is in compliance with a pre-determined performance standard. Challenge testing with *C. botulinum* is particularly appropriate for certain cooked products, such as products packaged under anaerobic and micro-aerophilic conditions (i.e. canned and modified atmosphere packed products) and products with a history of causing associated illness, such as products packed under oil.

Due to stringent F.D.A. regulations, testing of various foods using toxigenic *C. botulinum* strains require facilities that are certified for work with this organism. However, for certain applications, surrogate microorganisms are used in challenge studies in place of specific pathogens. For example, it is usually not possible or desirable to introduce pathogens such as toxigenic *C. botulinum* into a processing facility; therefore, surrogate microorganisms are used to test processing methods for effectiveness against *C. botulinum*.

Many surrogates are closely related to but not necessarily the same species as the target pathogen. Traditional examples include the use of *Clostridium sporogenes* as a proxy for *Clostridium botulinum* in inoculated pack studies, *Listeria innocua* as a surrogate for *L. monocytogenes*, and generic strains of *Escherichia coli* as substitutes for *E. Coli* O157:H7. An ideal surrogate, however, is a genetically stable strain of the target pathogen that retains all the characteristics of target pathogen, except for the target pathogen's virulence or toxicity. Thus, the ideal *Clostridium botulinum* surrogates would be nontoxigenic *C. botulinum* strains.

SUMMARY OF THE INVENTION

The inventors have developed novel nontoxigenic mutant strains of *Clostridium botulinum* 62A. Wild type *C. botulinum* strain 62A is a primary strain in standard food testing. Experiments with these nontoxigenic organisms could be readily performed in non-select agent laboratories, and the nontoxigenic organisms could be used for challenge studies validating a variety of food processing conditions and methods and in testing new food formulations.

Accordingly, the invention encompasses in a first aspect a mutant *Clostridium botulinum* strain 62A bacterium wherein the wild type botulinal neurotoxin gene is mutated by the insertion of an intron construct into the gene and wherein the insertion of the intron construct prevents the bacterium from synthesizing and secreting *botulinum* toxin. In certain preferred embodiments, the intron construct is inserted between nucleotides 580 and 581 of the botulinal neurotoxin gene having the nucleotide sequence set forth in SEQ ID NO:1. Preferably, the intron construct is inserted into the botulinal neurotoxin gene using ClosTron mutagenesis.

In certain such embodiments, the intron construct inserted into the botulinal neurotoxin gene is pMTL007:Cbot:bont-580s. Preferably, this intron construct is inserted between nucleotides 580 and 581 of the botulinal neurotoxin gene having the nucleotide sequence set forth in SEQ ID NO:1.

In another aspect, the invention encompasses bacterial cultures containing multiple mutant *Clostridium botulinum* bacteria as described above. In some such embodiments, the bacterial culture is biologically pure.

In a third aspect, the invention encompasses challenge cocktails for use in *Clostridium botulinum* challenge testing. Such challenge cocktails would contain one or more of the mutant *Clostridium botulinum* bacteria as described above.

In a fourth aspect, the invention encompasses methods of conducting a *Clostridium botulinum* challenge test of a food product or food processing steps. Such methods would include the steps of, (a) providing a challenge cocktail as described above; (b) preparing an inoculant from the challenge cocktail; (c) inoculating a food product with the inoculant; (d) sampling the inoculated food product to determine a level of *Clostridium botulinum* present in the inoculated food product; and (e) comparing the level of *Clostridium botulinum* present in the inoculated food product against a standard.

In certain embodiments, the method further includes the step of (f) determining from the comparison the resistance of the food product to *Clostridium botulinum* growth.

In some embodiments, the method may include the additional step of performing one or more food processing steps between the steps of inoculating a food product with the inoculant (step (c) above) and sampling the inoculated food product to determine a level of *Clostridium botulinum* present in the inoculated food product (step (d) above). Such food processing steps may include, but are not limited to, heating, irradiating, canning, storing the food with oil, or storing the food in a modified atmosphere. *botulinum* growth. sampling the inoculated food product to determine a level of *Clostridium botulinum* present in the inoculated food product. In such embodiments, it is preferred that the method include the additional step of determining from the comparison (step (e) above) the effectiveness of the food processing steps in inhibiting *Clostridium botulinum* growth.

In certain embodiments, the method is conducted over at least the shelf life of the food product.

The method can be used with a variety of food products, including without limitation dairy products, fruits, vegetables, and meats. In certain preferred embodiments, the method is used for testing canned food products, food products stored in a modified atmosphere, or food products stored in oil.

Other objects, advantages and features of the present invention will become apparent from the following specification taken in conjunction with the accompanying drawings.

BRIEF DESCRIPTION OF THE DRAWINGS

FIG. 5 is western analysis of neurotoxin expression in *C. botulinum* 62A wild type and mutant strains. (A) Coomassie stained SDS PAGE. (B) Western blot. Lanes 1-4, four individual mutant clones, WT—wild type strain. Purified *botulinum* neurotoxin (BoNT) was used as a standard. Abbreviations: BoNT/SC—*botulinum* neurotoxin/single chain, BoNT/LC—*botulinum* neurotoxin/light chain; BoNT/HC—*botulinum* neurotoxin/heavy chain. Protein samples were prepared from 96 hour cultures by trichloroacetic acid (TCA) precipitation as described in Bradshaw et al, 2004. Protein samples were reduced by addition of dithiothreitol to a final concentration of 10 mM. Proteins were separated by SDS-PAGE using 4-12% Bis-Tris NuPage Novex gels and transferred to a PVDF membrane. Membrane was reacted with a polyclonal affinity purified rabbit IgG specific for type A *botulinum* neurotoxin. The neurotoxin bands were visualized using a Western Breeze kit (Invitrogen).

DESCRIPTION OF THE PREFERRED EMBODIMENTS

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

In a first aspect, the present invention encompasses one or more mutant nontoxigenic *Clostridium botulinum* 62A bacteria and mutant bacterial strains made up of such bacteria. In the mutant bacteria of the invention, the botulinal neurotoxin gene is mutated by the insertion of an intron construct into the gene. The insertion of the intron construct prevents the mutant bacterium from synthesizing and secreting *botulinum* toxin.

In certain preferred embodiments, the wild type *Clostridium botulinum* strain 62A botulinal neurotoxin gene has the nucleotide sequence set forth in SEQ ID NO:1 and codes for the botulinal neurotoxin protein having the amino acid sequence set forth in SEQ ID NO:2. Preferably, the intron construct is inserted between nucleotides 580 and 581 of the wild type botulinal neurotoxin gene having the nucleotide sequence set forth in SEQ ID NO:1. Preferably, the intron construct is inserted using ClosTron mutagenesis, the clostridial gene inactivation system described in Heap et al. (2007) and Heap et al. (2009), which are both incorporated by reference herein.

As further described in the Example below, in making one such preferred embodiment, potential intron target sites in the toxin gene were first identified using a specific computer algorithm. PCR primers were then selected and a modified intron vector was generated for targeting *botulinum* neurotoxin gene between nucleotides 580 and 581 on the sense strand of the gene. This modified ClosTron plasmid was then introduced into the *C. botulinum* strain 62A by conjugation from *E. coli* donor strain CA434. Thiamphenicol resistant colonies were re-streaked on fresh plates to ensure their purity, and then plated on media supplemented with erythromycin to select for integrated intron clones. Single colonies of integrants were then screened for plasmid loss by thiamphenicol-sensitive phenotype. Next, correct insertion of the intron was verified by PCR and Southern hybridizations with a toxin gene probe and a probe for the erythromycin gene to confirm the presence of a single copy of the insertion element. The nontoxigenic phenotype of the mutant clones was confirmed by Western blot and mouse bioassay. Finally, several mutant clones were selected for further studies for comparison to the parental wild-type strain *C. botulinum* 62A in culture media to determine their growth and sporulation properties.

The invention further encompasses bacterial cultures comprising a plurality of the mutant *Clostridium botulinum* strain 62A bacteria described above. In certain embodiments, the bacterial cultures are biologically pure. In still other embodiments, the invention encompasses challenge cocktails for use in *Clostridium botulinum* challenge testing containing one or more of the mutated nontoxigenic *Clostridium botulinum* strain 62A bacteria described above.

In another aspect, the invention encompasses a method of using the mutant nontoxigenic strains of *C. botulinum* described above in microbiological challenge studies of foods and food products. For a general discussion of microbiological challenge studies, see Food and Drug Administration, Center for Food Safety and Applied Nutrition; U.S. Dept. of Agriculture, Food Safety and Inspection Service. 2001. Evaluation and Definition of Potentially Hazardous Foods, ch. 6, which is hereby incorporated by reference.

The first step in such a method is to select an appropriate challenge organism. Knowledge of the food formulation and history of the food (for example, association with known illness outbreaks and/or evidence of potential growth) is central to selecting the appropriate challenge pathogens. The *Clostridium botulinum* of the present invention would be useful as the challenge microorganism for the testing of a wide variety of food products, including without limitation fruits, vegetables, meats, dairy products, modified atmosphere packaged (MAP) products, canned products, and products packed in oil.

One practicing the invention may challenge a food product with a *C. botulinum* strain according to the invention or a mixture of multiple mutant nontoxigenic strains of *C. botulinum* (i.e., a "cocktail") in order to account for potential strain variation. It is preferable to incubate and prepare the challenge suspension under standardized conditions and format.

The inoculum level used in the microbiological challenge study depends on whether the objective of the study is to determine product stability and shelf life or to validate a step in a process designed to reduce microbial numbers. When validating a process lethality step for *C. botulinum* (such as heat processing, high pressure processing, or irradiation), it is usually necessary to use a high inoculum level (for example, $10^6$-$10^7$ cells/g of product) to demonstrate the extent of reduction in challenge organisms.

Bacterial spore suspensions may be stored in water under refrigeration or frozen in glycerol. Spore suspensions should be diluted in sterile water and heat-shocked immediately prior to inoculation. Spores of *C. botulinum* should be washed thoroughly prior to use and, if possible, the spores should be heat-shocked in the food to be studied. Quantitative counts on the challenge suspensions may be conducted to aid in calculating the dilutions necessary to achieve the target inoculum in the challenge product.

In certain embodiments, the microbiological challenge study extends for the duration of the desired shelf life of the product. It is even more desirable to challenge the product for its entire desired shelf life plus a margin beyond the desired shelf life, because it is important to determine what would happen if users would hold and consume the product beyond its intended shelf life. Some regulatory agencies require a minimum of data on shelf life plus at least one-third of the intended shelf life.

While the present invention has been described in several embodiments and examples, it is to be understood that the invention is not intended to be limited to the specific embodiments set forth above. Further, it is recognized that modifications may be made by one of skill in the art of the invention without departing from the spirit or intent of the invention and, therefore, the invention is to be taken as including all reasonable equivalents to the subject matter of the appended claims. All references cited herein are incorporated by reference for all purposes.

EXAMPLE

Production and Characterization of Nontoxigenic Mutant *C. botulinum*

This Example describes the method the inventors used to successfully produce the mutant nontoxigenic strain of *C. botulinum* 62A and describes methods used to characterize the mutant strain and to confirm its nontoxicity.

Introduction.

Figure 1:
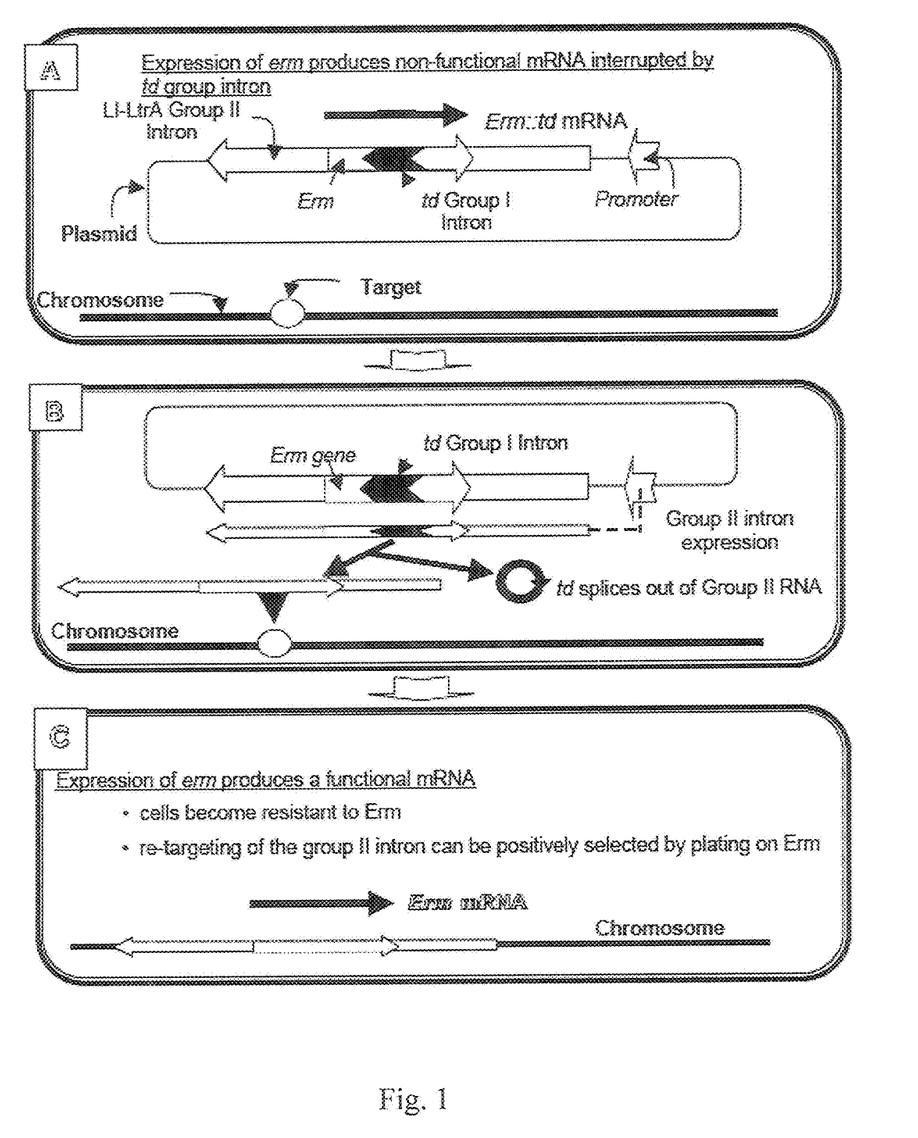
FIG. 1 is a schematic representation of the ClosTron mutagenesis system.

The knock-out of the *botulinum* neurotoxin gene was achieved using a ClosTron mutagenesis system that is based on the mobile group II intron from the ltrB gene of *Lactoccocus lactis* (Heap et al, 2007). The group II intron mediates its own mobility through the action of an intron-encoded reverse transcriptase (LtrA) and the excised lariat RNA. To facilitate isolation of mutants, the group II intron contains a resistance gene (ermB), which is itself interrupted by a self-splicing group I intron (FIG. 1A). The intron elements are arranged in such a way that only after successful insertion of the group II intron into its target is the nested group I intron spliced out, thus restoring the integrity of the antibiotic resistance gene (FIGS. 1B&C). Acquisition of the antibiotic resistance marker, referred as Retrotransposition-Activated Marker, RAM, is thereby strictly coupled to integration and thus can be used to positively select for integrational events.

Methods of Production.

Figure 2:
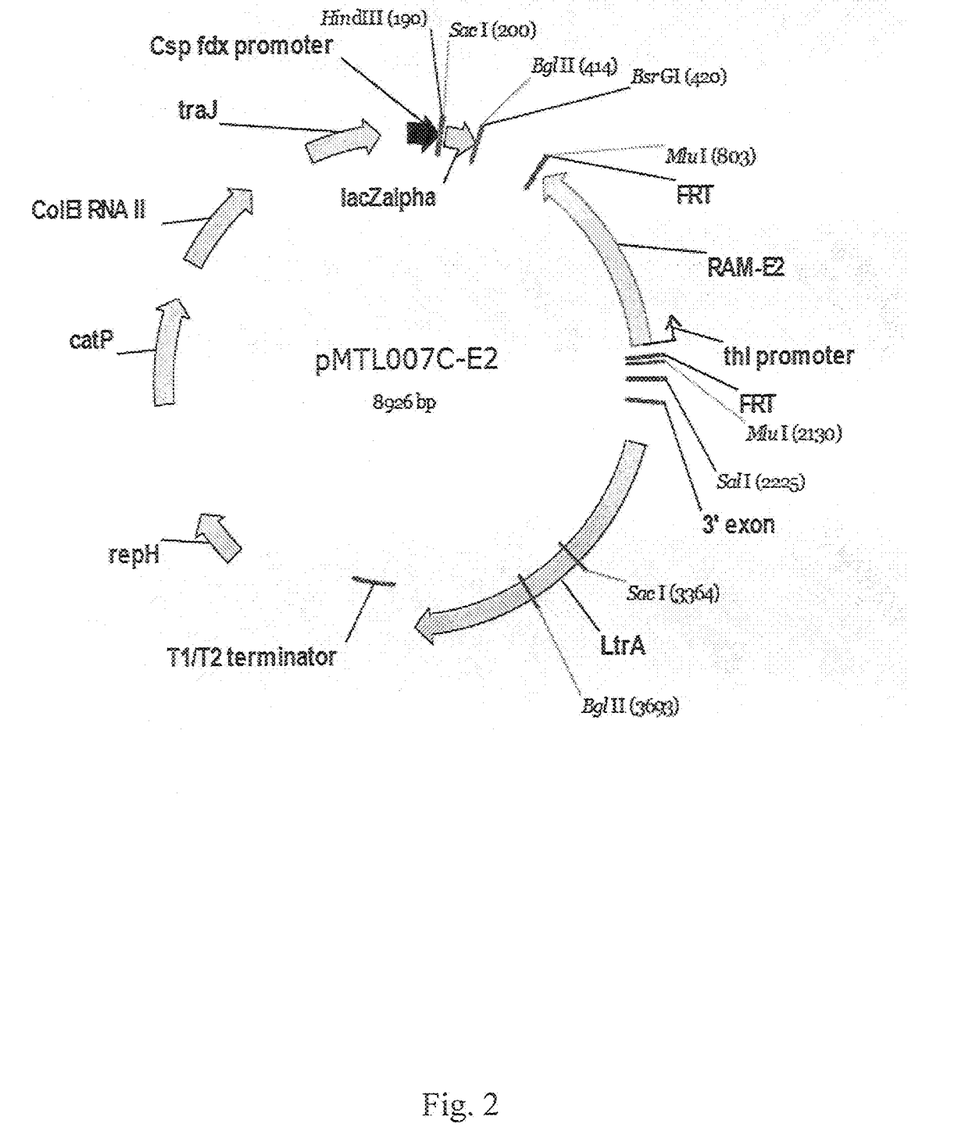
FIG. 2 is a plasmid map of pMTL007C-E2. The 350 by intron region generated by PCR was cloned into the vector between HindIII and BsrGI sites yielding a retargeted intron construct pMTL007:Cbot:bont-580s.

Potential intron target sites in the BoNT gene were identified using a specific computer algorithm (TargeTron web-based target identifier, Sigma Aldrich, St. Louis, Mo.). The software identifies potential target sites in the gene of interest and outputs a list of target sites and the sequences for oligonucleotide primers required to construct introns retargeted to the identified target sites. The primers were used in combination with template DNA supplied in the TargeTron Gene Knockout System kit (Sigma Aldrich, St. Louis, Missouri) to generate a ~350 by fragment. This 350 by variable intron region for the identified site was amplified by PCR, and after verification of the correct sequence, the fragment was inserted into the ClosTron vector pMTL007C-E2 (see FIG. 2), generating a retargeted intron construct, designated pMTL007:Cbot:bont-580s. The ClosTron method used to generate the intron constructs is further described in Heap et al (2009), pages 189-198, which is incorporated by reference herein.

The intron construct was then transferred to *C. botulinum* strain 62A by conjugation from *E. coli* donor strain CA434. After mating, the cell mixture was removed from the mating plates, diluted and plated on fresh media supplemented with cycloserine (selection for *C. botulinum*) and thiamphenicol (selection for pMTL007 vector). Thiamphenicol resistant colonies were re-streaked on fresh plates to ensure purity, and then plated on media supplemented with erythromycin to select for integrated intron clones. Single colonies of integrants were then screened for plasmid loss by thiamphenicol-sensitive phenotype.

Verifying Insertion of Intron Construct.

The insertion of the intron was verified by performing PCR (FIG. 3) and Southern hybridization (FIG. 4) with a probe for the RAM to confirm the presence of a single copy of the insertion element.

Figure 3:
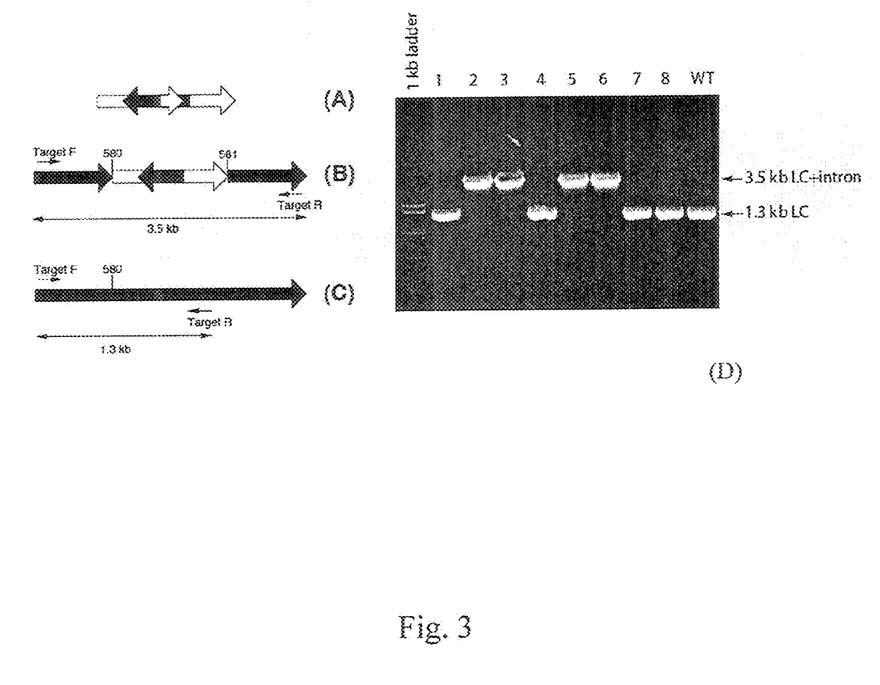
FIG. 3 shows mutant screening by PCR. Schematic representation shown of (A) Intron with RAM (as present in the vector), (B) Intron inserted into the target sequence, and (C) the *C. botulinum* neurotoxin gene. Location of the primers used in PCR are indicated as Target R and Target F; (D) shows ethidium bromide stained agarose gel electrophoresis results for the PCR product of eight putative mutant clones (lanes 1-8) and a wild type strain 62A (lane WT).

Four of the eight mutant clones (#2, 3, 5 and 6) analyzed produced a 3.5 kb PCR fragment as expected if the intron has been inserted into the target position in the *botulinum* neurotoxin gene (FIG. 3(D)). The other four mutant clones (#1, 4, 7 and 8) produced the same size fragment as the wild type strain, indicating that the intron had been inserted into some other location in the genome. The mutant clones #2, 3, 5 and 6 (designated in subsequent Figures as #1, 2, 3, and 4, respectively) were further analyzed by Southern hybridizations, Western blot and mouse bioassay to confirm their nontoxigenic phenotype.

Figure 4:
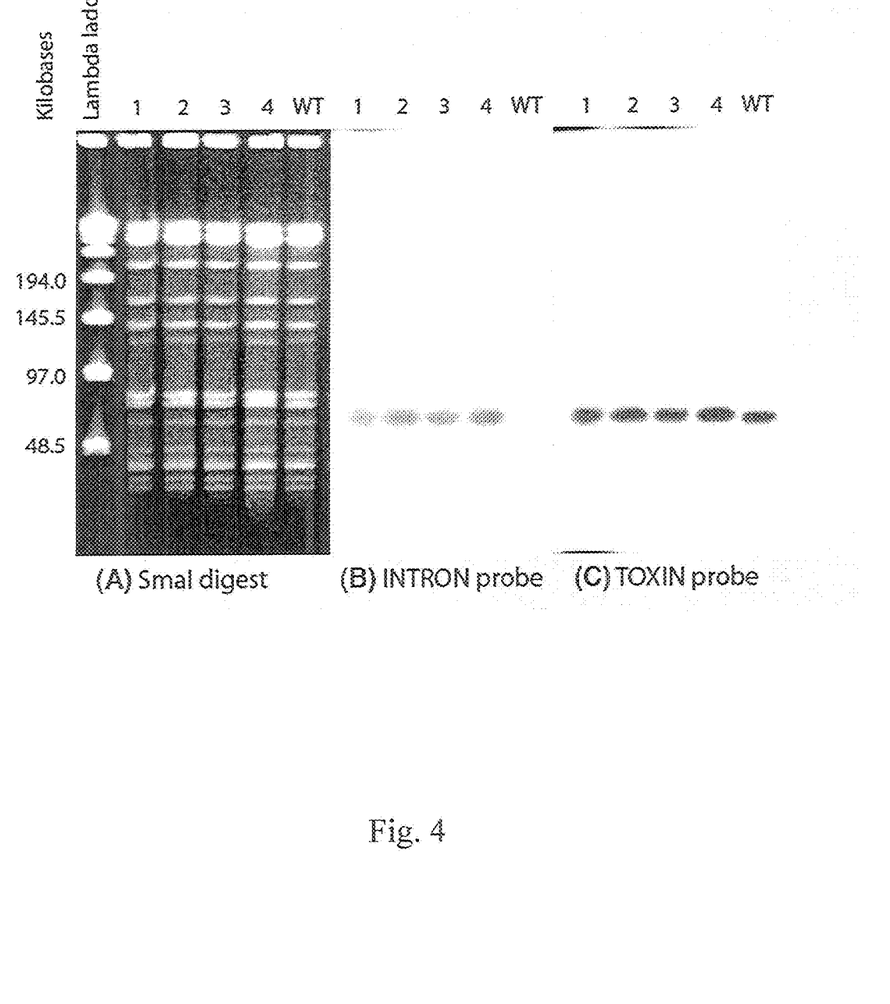
FIG. 4 is a pulsed field gel electrophoresis (PFGE) and a Southern hybridization analysis of the wild type *C. botulinum* strain 62A and toxin mutant strains. (A) PFGE of SmaI digested DNA. (B) Southern hybridization with the intron (erm) probe. (C) Southern hybridization with the *botulinum* neurotoxin probe. Lanes: 1-4, SmaI digests of four individual mutant clones, WT—SmaI digested wild type strain 62A; Lambda ladder—PFG marker (New England Biolabs). PFGE conditions: pulse time 1-20 s, 200V, 25 hours at 140 C (CHEFDRII, BioRad, Hercules, Calif.).

PFGE of SmaI digested DNA was performed for four mutant clones and wild type strains (FIG. 4A). All four mutant clones hybridized with the same size fragment using an intron specific probe (FIG. 4B). No hybridization was observed with the wild type strain. The membrane was stripped and rehybridized with the neurotoxin gene probe (FIG. 4C). The same band that hybridized with the intron probe also hybridized with all four mutants as well as with the wild type strain. Thus only one copy of the intron has been inserted into the *botulinum* neurotoxin gene in the mutant strains.

Nontoxicity of Mutant *C. botulinum* Strains.

Figure 5:
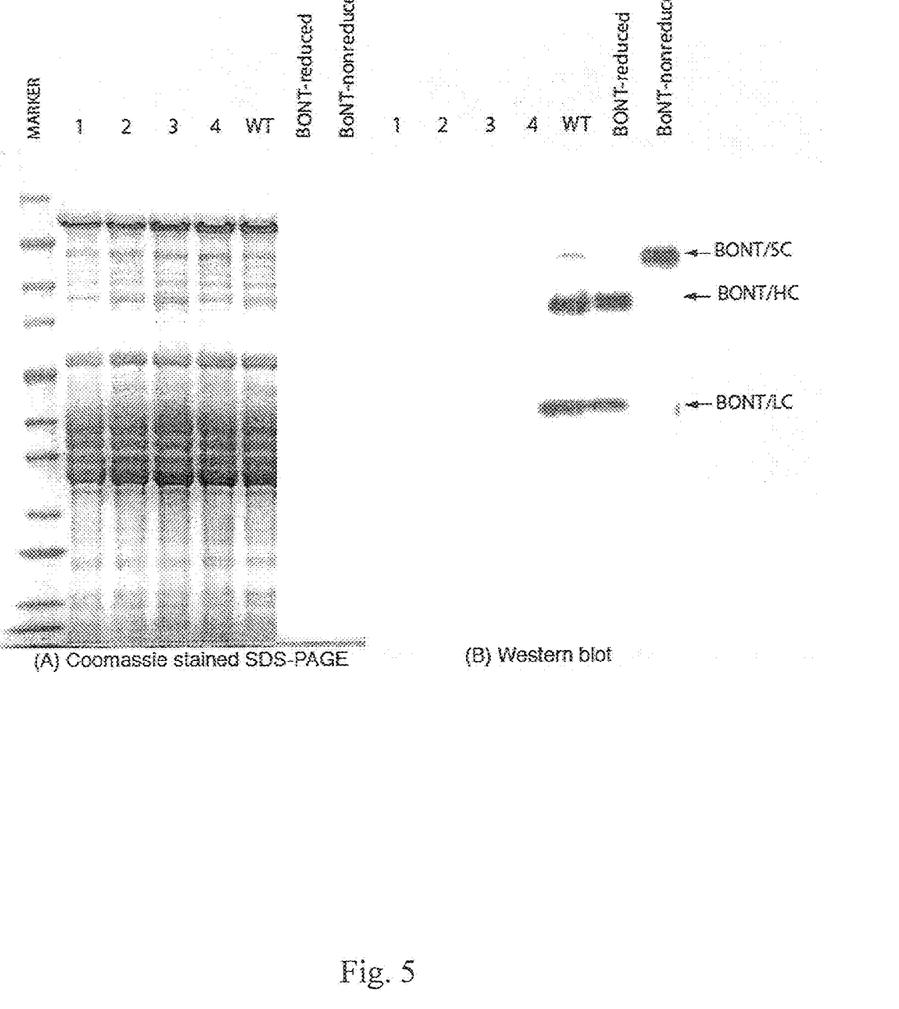

Finally, selected clones were analyzed by Western blot (FIG. 5) and mouse bioassay to confirm that the BoNT gene was inactivated and the selected clones were not producing and *botulinum* neurotoxin. None of the mutant clones reacted with the neurotoxin antibodies (FIG. 5). This indicates that the *C. botulinum* toxin mutant clones no longer produce *botulinum* neurotoxin.

Mouse bioassay by intraperitonneal (IP) injection was used to detect the presence of active *botulinum* neurotoxin in *C. botulinum* cultures. 0.5 ml of clarified 96 hour culture supernatants were injected (IP) into 2 mice per sample. Following injection, animals were observed for signs of botulism and the time of death noted. Minutes to death were then converted to IP LD50/ml of sample using standard curves previously prepared in our laboratory.

Mice injected with sample from the wild type strain died within 1 hour and 30 min, indicating that the strain contained ~$10^5$ LD50/ml of *botulinum* neurotoxin. Mice injected with culture supernatants from the mutant strains did not show any symptoms of botulism during 4 days. These results confirm that the mutant strains no longer produce *botulinum* neurotoxin.

Growth and Sporulation Properties of Wild Type and Mutant Strains.

Figure 6:
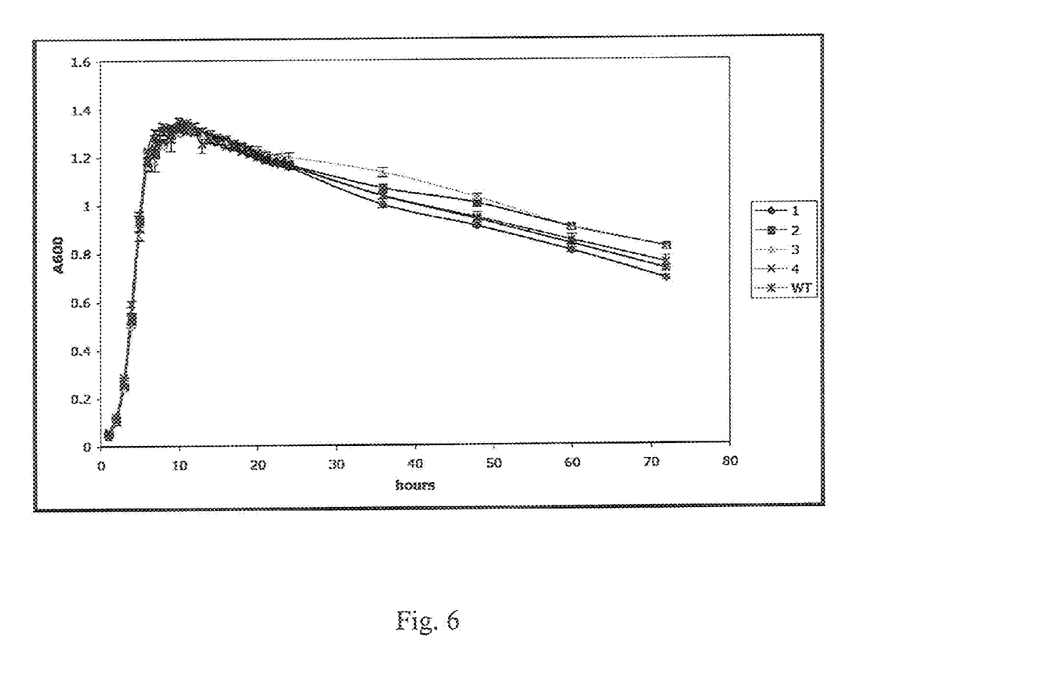
FIG. 6 shows growth curves of the four nontoxigenic mutant strains and a wild type *C. botulinum* strain 62A. The strains were inoculated in TPGY media (Bradshaw et al, 2004) in triplicate, grown at 37 degrees C. and 27 degrees C. (data not shown) and optical density measured as indicated.

The nontoxic mutant strains and a wild type strain exhibited similar growth characteristics and sporulation properties (FIG. 6). This indicates that the mutation of the present invention, while rendering the *C. botulinum* strain nontoxic, is otherwise similar to the toxic strain. Thus, we have confirmed the potential usefulness of the mutant strain of the invention in food challenge studies and related experiments.

While the present invention has been described in what is perceived to be the most practical and preferred embodiments and examples, it is to be understood that the invention is not intended to be limited to the specific embodiments set forth above. Further, it is recognized that modifications may be made by one of skill in the art of the invention without departing from the spirit or intent of the invention and, therefore, the invention is to be taken as including all reasonable equivalents to the subject matter of the appended claims. All references cited herein are incorporated by reference for all purposes.

Sequence Listing. Applicants are submitting as part of this Application a computer readable sequence listing txt file, which is incorporated by reference herein.

REFERENCES

1. Bradshaw et al, Regulation of neurotoxin complex expression in *Clostridium botulinum* strains 62A, Hall A-hyper, and NCTC 2916. 2004. Anaerobe 10: 321-333.
2. Heap et al, The ClosTron: a unique gene knock-out system for the genus *Clostridium*. 2007. J. Micr. Methods 70: 452-464.
3. Heap et al, The development of genetic knock-out systems for Clostridia, in Brüggemann and Gottschalk, ed., Clostridia: Molecular Biology in the Post-genomic Era (Norwich U.K.: Horizon Scientific Press) 2009; pages 179-198.

We claim:

1. A recombinant genetically modified *Clostridium botulinum* strain 62A bacterium comprising a genetic modification, wherein the genetic modification comprises insertion of mobile group II intron from ltrB gene of *Lactoccocus lactis* between nucleotides 580 and 581 of the botulinal neurotoxin gene having the nucleotide sequence set forth in SEQ ID NO:1.

2. A challenge cocktail for use in *Clostridium botulinum* challenge testing comprising the recombinant genetically modified *Clostridium botulinum* bacterium of claim 1.

3. A method of conducting a *Clostridium botulinum* challenge test of a food product or food processing steps, the method comprising:
   (a) inoculating a food product with a challenge cocktail according to claim 2;
   (b) sampling the inoculated food product to determine a level of *Clostridium botulinum* present in the inoculated food product; and
   (c) comparing the level of *Clostridium botulinum* present in the inoculated food product against a standard.

4. The method of claim 3, further comprising the step of (d) determining from the comparison the resistance of the food product to *Clostridium botulinum* growth.

5. The method of claim 3, further comprising the step of performing one or more food processing steps between the performance of steps (a) and (b).

6. The method of claim 5, wherein the one or more food processing steps are selected from heating, irradiating, canning, storing the food with oil, or storing the food in a modified atmosphere.

7. The method of claim 5, further comprising the step of (d) determining from the comparison the effectiveness of the food processing steps in inhibiting *Clostridium botulinum* growth.

8. The method of claim 3, wherein the method is conducted over at least the shelf life of the food product.

9. The method of claim 3, wherein the food product is a dairy product.

10. The method of claim 3, wherein the food product is a fruit, a vegetable, or a meat.

11. The method of claim 3, wherein the food product is canned, is stored in a modified atmosphere, or is stored in oil.

* * * * *

SEQUENCE LISTING

<160> NUMBER OF SEQ ID NOS: 2

<210> SEQ ID NO 1
<211> LENGTH: 3891
<212> TYPE: DNA
<213> ORGANISM: Clostridium botulinum

<400> SEQUENCE: 1

```
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttgggggtgga     360 agtacaaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gattttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta aagtaaatac taatgcctat tatgaaatga gtgggttaga agtaagcttt     780
gaggaactta gaacatttgg gggacatgat gcaaagttta tagatagttt acaggaaaac     840
```

```
gaatttcgtc tatattatta taataagttt aaagatatag caagtacact taataaagct         900
aaatcaatag taggtactac tgcttcatta cagtatatga aaaatgtttt taaagagaaa         960
tatctcctat ctgaagatac atctggaaaa ttttcggtag ataaattaaa atttgataag        1020
ttatacaaaa tgttaacaga gatttacaca gaggataatt ttgttaagtt ttttaaagta        1080
cttaacagaa aaacatattt gaattttgat aaagccgtat ttaagataaa tatagtacct        1140
aaggtaaatt acacaatata tgatggattt aatttaagaa atacaaattt agcagcaaac        1200
tttaatggtc aaaatacaga aattaataat atgaatttta ctaaactaaa aaattttact        1260
ggattgtttg aattttataa gttgctatgt gtaagaggga taataacttc taaaactaaa        1320
tcattagata aaggatacaa taaggcatta aatgatttat gtatcaaagt taataattgg        1380
gacttgtttt ttagtccttc agaagataat tttactaatg atctaaataa aggagaagaa        1440
attacatctg atactaatat agaagcagca gaagaaaata ttagtttaga tttaatacaa        1500
caatattatt taacctttaa ttttgataat gaacctgaaa atatttcaat agaaaatctt        1560
tcaagtgaca ttataggcca attagaactt atgcctaata tagaaagatt tcctaatgga        1620
aaaaagtatg agttagataa atatactatg ttccattatc ttcgtgctca agaatttgaa        1680
catggtaaat ctaggattgc tttaacaaat tctgttaacg aagcattatt aaatcctagt        1740
cgtgtttata catttttttc ttcagactat gtaaagaaag ttaataaagc tacggaggca        1800
gctatgtttt taggctgggt agaacaatta gtatatgatt ttaccgatga aactagcgaa        1860
gtaagtacta cggataaaat tgcggatata actataatta ttccatatat aggacctgct        1920
ttaaatatag gtaatatgtt atataaagat gattttgtag gtgctttaat attttcagga        1980
gctgttattc tgttagaatt tataccagag attgcaatac ctgtattagg tacttttgca        2040
cttgtatcat atattgcgaa taaggttcta accgttcaaa caatagataa tgctttaagt        2100
aaaagaaatg aaaaatggga tgaggtctat aaatatatag taacaaattg gttagcaaag        2160
gttaatacac agattgatct aataagaaaa aaaatgaaag aaactttaga aaatcaagca        2220
gaagcaacaa aggctataat aaactatcag tataatcaat atactgagga agagaaaaat        2280
aatattaatt ttaatattga tgatttaagt tcgaaactta atgagtctat aaataaagct        2340
atgattaata taaataaatt tttgaatcaa tgctctgttt catatttaat gaattctatg        2400
atcccttatg gtgttaaacg gttagaagat tttgatgcta gtcttaaaga tgcattatta        2460
aagtatatat atgataatag aggaacttta attggtcaag tagatagatt aaaagataaa        2520
gttaataata cacttagtac agatatacct tttcagcttt ccaaatacgt agataatcaa        2580
agattattat ctacatttac tgaatatatt aagaatatta ttaatacttc tatattgaat        2640
ttaagatatg aaagtaatca tttaatagac ttatctaggt atgcatcaaa aataaatatt        2700
ggtagtaaag taaattttga tccaatagat aaaaatcaaa ttcaattatt taatttagaa        2760
agtagtaaaa ttgaggtaat tttaaaaaat gctattgtat ataatagtat gtatgaaaat        2820
tttagtacta gcttttggat aagaattcct aagtattttg acagtataag tctaaataat        2880
gaatatacaa taataaattg tatggaaaat aattcaggat ggaaagtatc acttaattat        2940
ggtgaaataa tctggacttt acaggatact caggaaataa aacaaagagt agttttttaaa        3000
tacagtcaaa tgattaatat atcagattat ataaacagat ggattttttgt aactatcact        3060
aataatagat taaataactc taaaatttat ataaatggaa gattaataga tcaaaaacca        3120
atttcaaatt taggtaatat tcatgctagt aataatataa tgtttaaatt agatggttgt        3180
```

-continued

```
agagatacac atagatatat ttggataaaa tattttaatc tttttgataa ggaattaaat    3240
gaaaaagaaa tcaaagattt atatgataat caatcaaatt caggtatttt aaaagacttt    3300
tggggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttattta aattcaagtt tgtataggggg acaaaatttt    3480 attataaaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

-continued

```
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Met Phe Leu Gly Trp Val Glu
            595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
```

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Thr Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
        1025                1030                1035

Lys Pro Ile Ser Asn Leu Gly Asn Ile His Ala Ser Asn Asn Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080

Ile Lys Asp Leu Tyr Asp Asn Gln Ser Asn Ser Gly Ile Leu Lys

-continued

```
            1085                1090                1095
Asp Phe Trp Gly Asp Tyr Leu Gln Tyr Asp Lys Pro Tyr Tyr Met
        1100                1105                1110
Leu Asn Leu Tyr Asp Pro Asn Lys Tyr Val Asp Val Asn Asn Val
        1115                1120                1125
Gly Ile Arg Gly Tyr Met Tyr Leu Lys Gly Pro Arg Gly Ser Val
        1130                1135                1140
Met Thr Thr Asn Ile Tyr Leu Asn Ser Ser Leu Tyr Arg Gly Thr
        1145                1150                1155
Lys Phe Ile Ile Lys Lys Tyr Ala Ser Gly Asn Lys Asp Asn Ile
        1160                1165                1170
Val Arg Asn Asn Asp Arg Val Tyr Ile Asn Val Val Val Lys Asn
        1175                1180                1185
Lys Glu Tyr Arg Leu Ala Thr Asn Ala Ser Gln Ala Gly Val Glu
        1190                1195                1200
Lys Ile Leu Ser Ala Leu Glu Ile Pro Asp Val Gly Asn Leu Ser
        1205                1210                1215
Gln Val Val Val Met Lys Ser Lys Asn Asp Gln Gly Ile Thr Asn
        1220                1225                1230
Lys Cys Lys Met Asn Leu Gln Asp Asn Asn Gly Asn Asp Ile Gly
        1235                1240                1245
Phe Ile Gly Phe His Gln Phe Asn Asn Ile Ala Lys Leu Val Ala
        1250                1255                1260
Ser Asn Trp Tyr Asn Arg Gln Ile Glu Arg Ser Ser Arg Thr Leu
        1265                1270                1275
Gly Cys Ser Trp Glu Phe Ile Pro Val Asp Asp Gly Trp Gly Glu
        1280                1285                1290
Arg Pro Leu
        1295
```

UNITED STATES PATENT AND TRADEMARK OFFICE
CERTIFICATE OF CORRECTION

PATENT NO. : 10,253,074 B2
APPLICATION NO. : 12/550692
DATED : April 9, 2019
INVENTOR(S) : Eric A. Johnson et al.

It is certified that error appears in the above-identified patent and that said Letters Patent is hereby corrected as shown below:

In the Specification

Column 3, Line 20, "350 by" should be --350 bp--.

Column 6, Line 26, "~350 by" should be --~350 bp--.

Column 6, Line 26, "350 by" should be --350 bp--.

Signed and Sealed this
Eighteenth Day of June, 2019

Andrei Iancu
*Director of the United States Patent and Trademark Office*